US005910323A

United States Patent [19]

Lajoie et al.

[11] Patent Number: 5,910,323

[45] Date of Patent: Jun. 8, 1999

[54] INSECTICIDE COMPOSITIONS

[75] Inventors: M. Stephen Lajoie, Basking Ridge; Amy L. Joseph, Hopewell, both of N.J.; Keith A. Jones, Yardley, Pa.; Anthony E. Winston, East Brunswick, N.J.

[73] Assignee: Church & Dwight Co., Inc.

[21] Appl. No.: 08/139,057

[22] Filed: Oct. 21, 1993

Related U.S. Application Data

[63] Continuation of application No. 07/881,694, May 12, 1992, abandoned.

[51] Int. Cl.[6] .......................... A01N 59/00; A01N 47/30; A01N 31/16; A01N 31/02

[52] U.S. Cl. .......................... 424/717; 424/715; 424/716; 514/53; 514/75; 514/122; 514/132; 514/477; 514/517; 514/521; 514/531; 514/574; 514/594; 514/709; 514/710; 514/734; 514/738; 514/762; 514/766; 514/772; 514/724; 71/DIG. 1

[58] Field of Search .................................... 514/594, 734, 514/53, 75, 122, 132, 477, 517, 521, 531, 574, 709, 710, 738, 762, 766, 772, 724; 424/715, 716, 717; 71/DIG. 1

[56] References Cited

U.S. PATENT DOCUMENTS

| | | | |
|---|---|---|---|
| 482,403 | 9/1892 | Carter | 424/717 |
| 1,044,452 | 11/1912 | Halland | 424/715 |
| 3,639,633 | 2/1972 | Buchanan | 514/477 |
| 3,933,908 | 1/1976 | Wellinga et al. | 564/44 |
| 4,324,799 | 4/1982 | Koch et al. | 424/301 |
| 4,599,233 | 7/1986 | Misato et al. | 424/717 |
| 4,933,000 | 6/1990 | Somlo | 504/212 |
| 4,960,784 | 10/1990 | Lahm | 514/403 |
| 5,004,614 | 4/1991 | Staniforth | 424/466 |

FOREIGN PATENT DOCUMENTS

| | | |
|---|---|---|
| 2013918 | 10/1990 | Canada . |
| 52-07438 | 1/1977 | Japan . |
| 53-96319 | 8/1978 | Japan . |
| 60-153785 | 8/1985 | Japan . |

OTHER PUBLICATIONS

Chemical Abstracts 92:35946 (1980).

Farm Chemicals Handbook 1987, Ohio, Meister Publishing Co., 1987, p. C165.

The Merck Index, 10th ed., NJ, Merck & Co., Inc., 1983, pp. 818–819.

*Primary Examiner*—John Pak
*Attorney, Agent, or Firm*—Irving Fishman

[57] ABSTRACT

This invention provides a novel aqueous pesticide formulation having a fungicidal bicarbonate-containing inorganic salt ingredient which enhances the efficacy of an insecticidal ingredient for treatment of cultivated crops. An invention pesticide formulation also contains a water-soluble organic compound which functions as a compatibility enhancing ingredient in the aqueous pesticide formulation, and improves the spreadability and adhesiveness of the composition ingredients when applied to foliage.

17 Claims, No Drawings

INSECTICIDE COMPOSITIONS

This application is a continuation of application Ser. No. 07/881,694, filed May 12, 1992 now abandoned.

BACKGROUND OF THE INVENTION

A wide variety of ornamental and agricultural plants are susceptible to infestation by insects and arachnids. The pests inflict damage by consuming foliage and roots, withdrawing juices from the plants, secreting toxins, and infecting with diseases.

Field crops which require protection from pests include such valuable crops as soybeans, corn, peanuts, cotton, alfalfa and tobacco. In addition, vegetables such as tomatoes, potatoes, sugar-beets, carrots, and the like, and nuts, ornamentals, apples, peaches, peas, citrus fruit and grape also require protection from the ravages of such pests.

Insects which are difficult to control include those which inhabit the soil and cause destruction of the root systems of valuable agricultural crops. Corn rootworms are the larvae of several beetle species of the genus Diabrotica. The adult beetles lay their eggs in the soil of a maturing corn crop. The eggs lay dormant in the soil until the following spring, then they hatch in response to favorable soil temperatures and the larvae feed on the roots of young corn plants causing reduction in yield.

A broad scope of insecticide compounds have been developed to combat insects which are harmful to agricultural and horticultural plants. Illustrative of insecticide compositions are those described in U.S. Pat. Nos. 3,217,037; 3,506,698; 3,576,834; 3,636,111; 3,755,364; 3,875,232; 4,028,413; 4,128,581; 4,415,743; 4,640,927; 4,804,653; 4,839,349; 5,010,068; 5,087,456; 5,087,456; 5,096,928; and references cited therein.

There remains a continuing need for the development of new and more effective insecticides which possess contact or systemic insecticidal activity for the protection of cultivated plants, with a minimum of phytotoxic side effects.

Accordingly, it is an object of this invention to provide a biocide composition which is a blend of inorganic and organic compounds exhibiting insecticidal properties.

It is another object of this invention to provide an insecticide composition which is a dry blend of ingredients which include a bicarbonate salt which enhances the biocidal activity of an insecticide ingredient.

Other objects and advantages of the present invention shall become apparent from the accompanying description and examples.

DESCRIPTION OF THE INVENTION

One or more objects of the present invention are accomplished by the provision of an insecticide composition which is a dry blend formulation comprising (1) an ingredient selected from alkali metal and ammonium bicarbonates; (2) a compatibility enhancing ingredient selected from water-soluble organic compounds which are in solid form at a temperature below about 10° C.; and (3) an organic insecticide ingredient.

In another embodiment this invention provides an aqueous insecticide formulation having a content comprising (1) an ingredient selected from alkali metal and ammonium bicarbonates; (2) a compatibility enhancing ingredient selected from water-soluble organic compounds which are in solid form at a temperature below about 10° C.; and (3) an organic insecticide ingredient.

The inorganic salt ingredient is selected from compounds which include sodium bicarbonate, potassium bicarbonate, lithium bicarbonate and ammonium bicarbonate. In a further embodiment, the inorganic salt ingredient can include an additional compound selected from sodium carbonate, potassium carbonate, lithium carbonate and ammonium carbonate.

The inorganic salt ingredient typically will comprise between about 10–80 weight percent, based on the weight of dry blend formulation.

Illustrative of inorganic salt ingredients in a formulation are sodium, potassium, lithium or ammonium bicarbonate, or mixtures such as sodium bicarbonate and potassium bicarbonate; sodium bicarbonate and ammonium bicarbonate; potassium bicarbonate and ammonium bicarbonate; sodium bicarbonate, potassium bicarbonate and ammonium bicarbonate; sodium bicarbonate and potassium carbonate; potassium bicarbonate and potassium carbonate; and the like.

Multiple inorganic salt compounds can be utilized in a broad range of molar quantities relative to each other. The molar quantity of a carbonate salt compound normally is determined by pH control considerations when aqueous formulations are prepared. The content of a carbonate salt compound can be varied to control the pH at a desired level in the range of 7.5–12.

A compatibility enhancing ingredient of the present invention insecticide compositions is a water-soluble organic compound which is in solid form at a temperature below about 10° C. Suitable compounds include acetamide, acetylurea, alanine, aminoquanidine, aminomalonate salt, aminopyridine, arabinose, benzenesulfonate salt, benzoate salt, citraconate salt, citrate salt, crotonate salt, cyclohexanol, dihydroxyacetone, dihydroxyacetone phosphate salt, dihydroxybenzene, dimethylurea, ethanolamine, ethyl alaninate, ethyl arsonate, ethylglycine, ethylurea, ethylenedisulfonate salt, ethyleneurea, paraformaldehyde, fucose, glutamate salt, glycerol, glycerol nitrate, glycerol phosphate salt, glycogen, glycolic aldehyde, glyoxal, guanidine, hexamine, mannitol, fructose, glucose, hydroxyurea, lactate salt, lactose, lysine, maleic amide, malonate salt, maltose, maltodextrin, methoxypyridine, methyl acetate, methyl carbamate, methyl ethyl sulfone, methyl glucoside, methylhydantoin, methylinositol, methylthiourea, methyluracil, methylurea, methylenedisulfonate salt, muconate salt, naphtholdisulfonate salt, nitrobenzoate salt, nitropentanediol, nitrophenol salt, nitrourethane, pentaglycerol, phenol, phenylenediamine, polydextrose, propionamide, propyl carbamate, propylurea, purine, pyrazine, pyrimidine, ribose, saccharate salt, sarcosinate salt, semicarbazide, sorbate salt, succinimide, sucrose, tartarate salt, tetrahydrobenzoate salt, tetrahydroquinoline, tetrazine, thiourea, threonine, triaminobenzene, triazole, triethylphosphine oxide, triethylenetetramine, trihydroxybenzene, trimethylurea, urea, xylenol, xylose, xylylene glycol, polyvinylpyrrolidone, sodium carboxymethylcellulose, xanthan gum, guar gum, locust bean gum, gum acacia, gum tragacanth, potassium alginate, potato agar, and the like.

The compatibility enhancing ingredient is incorporated in a quantity between about 0.5–20 weight percent, based on the weight of ingredients in a dry blend insecticide composition.

The term "water-soluble" as employed herein refers to a compatibility enhancing organic compound which has a solubility of at least about one gram per 100 grams of water at 25° C.

The insecticidal ingredient of an invention insecticide composition is included in a quantity which will provide a concentration between about 100 ppm and 10 weight percent of the medium which is being applied to seeds, plants, trees, harvested crops, soil, and the like. The medium can be a dry blend mixture or an aqueous spraying formulation.

The insecticide ingredient can be selected from a wide variety of organic compounds or mixtures which are known and used in agriculture and horticulture applications, such as those listed in Agricultural Chemicals, Book I, Insecticides, 1989 Revision (W. T. Thomson, Thomson Publications, Fresno, Calif. 93791).

The general categories of insecticidal-active organic compounds include chlorinated hydrocarbon derivatives, phosphorated derivatives, pyrethroids, acylureas, and the like.

The chlorinated hydrocarbon insecticides usually act as stomach and contact poisons affecting the nervous system. They are persistent in the environment and tend to accumulate in animal fatty tissue, as exemplified by DDT and chlordane.

The organic phosphates generally are contact and/or stomach poisons. They are less persistent in the environment than the chlorinated hydrocarbons. They are toxic since they generally are cholinesterase inhibitors, which interfere with nerve impulse transmission. Most of these compounds are characterized by relatively low $LD_{50}$ values, although the value for malathion is 1400. Parathion is one of the best known organic phosphate systemic insecticides, and is considered a dangerous material to handle.

The carbamates are similar in action to the organic phosphate insecticides. These insecticides usually are not magnified in the food chain, and are characterized by rapid breakdown.

The synthetic pyrethroids react well with synergists and exhibit relatively low mammalian toxicity. Generally they break down rapidly and leave little residue.

Illustrative of other insecticidal compounds are chlorfluazuron, chlorpyrifos, chlorpyrifos methyl, bromophos, diazinon, malathion, trichlorfon, dimethoate, phorate, lindane, toxaphene, diflubenuron, methomyl, propoxur, carbaryl, cyhexatin, cypermethrin, permethrin, fenvalerate, dicofol, tetradifon, propargite, and the like.

Invention insecticide compositions can be in the form of dusting powders or granules, which optionally can include a solid diluent such as bentonite, calcium carbonate, magnesia, gypsum, kieselguhr, diatomaceous earth, and the like. Granules can be formed by impregnating pellets of filler with the insecticide composition ingredients, or by pelleting a dry blend insecticide composition in admixture with a powdered filler.

An invention insecticide composition also can be in the form of a dispersible powder in combination with a surfactant to facilitate dispersion of the powder in an aqueous medium. The surfactant is incorporated in an insecticide composition in a quantity between about 1–20 weight percent, based on the weight of water-insoluble ingredients.

The surfactant can be a cationic, anionic or nonionic type, or a mixture thereof. Suitable surfactants include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; and the like.

The ingredients in an invention insecticide composition can be selected to include nitrogen, phosphorus and potassium elements, in a ratio that allows the composition to function as a fertilizer in addition to its function as an insecticide, when applied to cultivated crops.

An invention insecticide composition can include one or more other biologically active ingredients, such as those which exhibit herbicidal, fungicidal or plant growth regulating activity.

The amount of the pesticidally-active ingredient in an invention composition depends upon the specific pest to be combatted, as well as upon the specific insecticidal ingredient and formulation being employed, the method of applying the formulation, and the locus of treatment. Spray dilutions may be as low as a few parts per million.

When plants constitute the locus of treatment, concentration per unit area may range between about 0.01–5.0 pounds per acre, with concentrations of between about 0.1–10 pounds per acre being employed for crops such as corn, tobacco, rice, and the like.

When soil is the locus of treatment, the pesticide ingredient is applied at a rate of about 0.25–12 pounds per acre.

An insecticide composition of the present invention has a novel combination of properties for the practice of pesticide control in agricultural and horticultural applications.

A compound of the inorganic salt ingredient exhibits fungicidal properties, and the efficacy of the insecticide ingredient is enhanced by the presence of the inorganic salt ingredient. A lesser quantity of insecticide ingredient then can be employed to achieve a desired degree of pest control.

A present invention insecticide composition can be formulated to exhibit little or no phytotoxicity, or to minimize the toxic effects of salt stress on plants by the inorganic salt ingredient.

A significant feature of a present invention insecticide composition is the inclusion of a compatibility enhancing agent as an essential ingredient. Migration and settling of solid ingredients is minimized, and a dry blend formulation has a more uniformly distributed content because of the presence of the compatibility enhancing ingredient. An aqueous insecticidal formulation has exceptional long term stability, without phase separation and precipitation of solids.

As a further advantage, a present invention aqueous insecticide formulation has improved spreadability and adhesiveness when applied to plant foliage, and resists post-application insecticide drift. An applied formulation also exhibits humectant properties on coated foliage, and increased insecticidal efficacy because of the presence of the compatibility enhancing ingredient.

The following examples are further illustrative of the present invention. The components and specific ingredients are presented as being typical, and various modifications can be derived in view of the foregoing disclosure within the scope of the invention.

EXAMPLE I

This Example illustrates the preparation of an insecticide dusting powder in accordance with the present invention.

A blend of the following ingredients is prepared:

| | Parts |
|---|---|
| $KHCO_3$ | 30 |
| methomyl | 5 |

-continued

| | Parts |
|---|---|
| mannitol | 5 |
| talc | 65 |

The formulated blend is milled to provide a powder with a particle size of less than 0.5 micron.

EXAMPLE II

This Example illustrates the preparation of an acylurea-containing agricultural insecticide composition.

A blend of the following ingredients is prepared as a wettable powder formulation:

| | Parts |
|---|---|
| $NaHCO_3$ | 30 |
| diflubenzuron | 6 |
| dihydroxybenzene | 2 |
| sodium lignosulfonate | 2 |
| kaolin | 30 |

The formulation is dispersed in water (20% by weight solids) to form a stock medium. Aliquots of the aqueous formulation are diluted with water to 50, 100 and 500 ppm of diflubenzuron respectively, and tested for insecticidal activity.

The formulation is effective for 100 percent control of southern corn rootworm (*Diabrotica undecimpunctata*) larvae and tobacco budworm (*Heliothis virescens*) larvae.

EXAMPLE III

This Example illustrates the preparation of a granulated insecticide composition which has a high suspension capacity in water.

A mixture of the following ingredients is prepared:

| | Parts |
|---|---|
| toxaphene | 60 |
| $NaHCO_3$ | 10 |
| $KHCO_3$ | 5 |
| hexamine | 2 |
| sodium lignosulfonate | 20 |

The mixture is dispersed in water, and spray-dried at 180° C. The resulting granules have a 70% suspension capacity in water.

EXAMPLE IV

This Example illustrates the preparation of insecticide composition tablets which rapidly disintegrate and disperse in water.

| | Parts |
|---|---|
| permethrin | 40 |
| $NaHCO_3$ | 35 |
| citric acid | 12 |
| Lomar PWA 10[(1)] | 10 |
| glyoxal | 2 |
| sodium lignosulfonate | 1 |

-continued

The ingredients are blended, and formed into tablets which disintegrate and disperse in water within about five minutes at 25° C.

[(1)]sodium salt of alkylarylsulfonate condensation product (Jacques Wolf & Co.)

EXAMPLE V

This Example illustrates the preparation of a water-dilutable liquid concentrate insecticide composition.

A liquid concentrate is prepared from the following ingredients:

| | Parts |
|---|---|
| propargite | 10 |
| $NaHCO_3$ (300 mesh) | 35 |
| $KHCO_3$ (300 mesh) | 35 |
| oleic acid monoglyceride | 30 |
| glyceryl monooctanoate | 10 |
| glycerol | 5 |

The ingredients are admixed and heated at 40° C. to form a concentrated liquid suspension. When the suspension is diluted with water, it forms a stable emulsion which has utility as an insecticide spray in agricultural applications for control of mites.

EXAMPLE VI

This Example illustrates the preparation of an aqueous insecticidal formulation stabilized with a nonionic surfactant phosphate ester salt.

| | Parts |
|---|---|
| parathion | 22 |
| $KHCO_3$ | 10 |
| $NH_4CO_3$ | 10 |
| polyoxyethylene (7.6 mol)-phenylphenol ether phosphate diethanol-amine salt | 5 |
| sucrose | 5 |
| water | 60 |

The ingredients are added to the water medium with high speed stirring to form a stable emulsion suitable for spraying of plant foliage to control insects.

EXAMPLE VII

This Example illustrates the preparation of an acaricide-fertilizer composition for application to cultivated fields.

A blend of the following ingredients is prepared:

| | Parts |
|---|---|
| melamine | 40 |
| urea | 30 |
| potassium glycerol phosphate | 20 |
| tetradifon | 5 |
| $KHCO_3$ | 15 |

Granules are prepared by tumbling the blend, spraying added water to form tacky solids, and then drying the granulated product.

What is claimed is:

1. An aqueous pesticide formulation having a content comprising (1) between about 10–80 weight percent of a fungicidal ingredient selected from the group consisting of alkali metal and ammonium bicarbonates, based on the weight of ingredients; (2) between about 0.5–20 weight percent of a water-soluble polyhydroxy compatibility enhancing ingredient which is in solid form at a temperature below about 10° C., based on the weight of ingredients; (3) between about 0.01–10 weight percent of an insecticidal ingredient, based on the formulation weight; and (4) between about 1–20 weight percent of a surfactant ingredient, based on the weight of water-soluble ingredients.

2. An aqueous pesticide formulation in accordance with claim 1 which exhibits fungicidal and enhanced insecticidal properties in agricultural and horticultural applications.

3. An aqueous pesticide formulation in accordance with claim 1 wherein the fungicidal bicarbonate ingredient is sodium bicarbonate.

4. An aqueous pesticide formulation in accordance with claim 1 wherein the compatibility enhancing ingredient is dihydroxybenzene.

5. An aqueous pesticide formulation in accordance with claim 1 wherein the insecticidal ingredient is diflubenzuron.

6. An aqueous pesticide formulation in accordance with claim 1 wherein the surfactant ingredient is sodium lignosulfonate.

7. An aqueous pesticide formulation in accordance with claim 1 which is diluted with water to an insecticidal ingredient content between about 0.005–0.05 weight percent.

8. A method of controlling fungal disease and insect damage in agricultural and horticultural applications which comprises applying to cultivated crops an aqueous pesticide formulation having a content comprising (1) between about 10–80 weight percent of a fungicidal ingredient selected from the goup consisting of alkali metal and ammonium bicarbonates, based on the weight of ingredients; (2) between about 0.5–20 weight percent of a water-soluble polyhydroxy compatibility enhancing ingredient which is in solid form at a temperature below about 10° C., based on the weight of ingredients; (3) between about 0.01–10 weight percent of an insecticidal ingredient, based on the formulation weight; and (4) between about 1–20 weight percent of a surfactant ingredient, based on the weight of water-insoluble ingredients.

9. A method in accordance with claim 8 wherein the fungicidal bicarbonate ingredient is sodium bicarbonate.

10. A method in accordance with claim 8 wherein the compatibility enhancing ingredient is dihydroxybenzene.

11. A method in accordance with claim 8 wherein the insecticidal ingredient is diflubenzuron.

12. A method in accordance with claim 8 wherein the surfactant ingredient is sodium lignosulfonate.

13. A method in accordance with claim 8 in which the formulation is diluted with water to an insecticidal ingredient content between about 0.005–0.05 weight percent before application.

14. A method of controlling southern corn rootworm larvae which comprises applying to a corn crop an aqueous pesticide formulation having a content comprising (1) between about 10–80 weight percent of sodium bicarbonate, based on the weight of ingredients; (2) between about 0.5–20 weight percent of dihydroxybenzene, based on the weight of ingredients; (3) between about 0.01–10 weight percent of diflubenzuron, based on the formulation weight, and (4) between about 1–20 weight percent of sodium lignosulfonate, based on the weight of water-insoluble ingredients.

15. A method in accordance with claim 14 in which the formulation is diluted with water to a diflubenzuron content between about 0.005–0.05 weight percent before application.

16. A method of controlling tobacco budworm larvae which comprises applying to a tobacco crop an aqueous pesticide formulation having a content comprising (1) between about 10–80 weight percent of sodium bicarbonate, based on the weight of ingredients; (2) between about 0.5–20 weight percent of dihydroxybenzene, based on the weight of ingredients; (3) between about 0.01–10 weight percent of diflubenzuron, based on the formulation weight; and (4) between about 1–20 weight percent of sodium lignosulfonate, based on the weight of water-insoluble ingredients.

17. A method in accordance with claim 16 in which the formulation is diluted with water to a diflubenzuron content between about 0.005–0.05 weight percent before application.

* * * * *